United States Patent [19]

Maurer et al.

[11] Patent Number: 5,064,818
[45] Date of Patent: Nov. 12, 1991

[54] PESTICIDAL PYRIMIDINYL (THIONO)(THIO)-PHOSPHORIC (PHOSPHONIC)ACID (AMIDE) ESTERS

[75] Inventors: Fritz Maurer, Wuppertal; Jürgen Hartwig, Leverkusen, both of Fed. Rep. of Germany; Benedikt Becker, Pineta di Laives, Italy

[73] Assignee: Bayer Aktiengesellschaft, Leverkusen, Fed. Rep. of Germany

[21] Appl. No.: 510,363

[22] Filed: Apr. 16, 1990

[30] Foreign Application Priority Data

May 4, 1989 [DE] Fed. Rep. of Germany ....... 3914714

[51] Int. Cl.$^5$ .................. A01N 57/16; A01N 57/24; C07F 9/6512
[52] U.S. Cl. .................................. 514/86; 544/243; 544/303; 544/313
[58] Field of Search ........................ 544/243; 514/86

[56] References Cited

U.S. PATENT DOCUMENTS

| | | | |
|---|---|---|---|
| 3,205,231 | 9/1965 | Fest et al. | 544/243 |
| 4,014,882 | 3/1977 | Sharpe | 544/243 |
| 4,225,594 | 9/1980 | Maurer et al. | 514/86 |
| 4,489,068 | 12/1984 | De Vries et al. | 514/86 |
| 4,575,499 | 3/1986 | Reifschneider | 514/86 |
| 4,692,524 | 9/1987 | Hässig | 544/303 |
| 4,769,364 | 9/1988 | Maurer et al. | 514/86 |

FOREIGN PATENT DOCUMENTS

| | | | |
|---|---|---|---|
| 0224217 | 6/1987 | European Pat. Off. | 544/243 |
| 0279259 | 8/1988 | European Pat. Off. | |
| 2804889 | 8/1979 | Fed. Rep. of Germany | 514/86 |
| 2230651 | 12/1974 | France | |

Primary Examiner—Diana G. Rivers
Attorney, Agent, or Firm—Sprung Horn Kramer & Woods

[57] ABSTRACT

Insecticidal, acaricidal and nematocidal pyrimidinyl(thiono)(thio)-phosphoric(phosphonic) acid (amide) esters of the formula

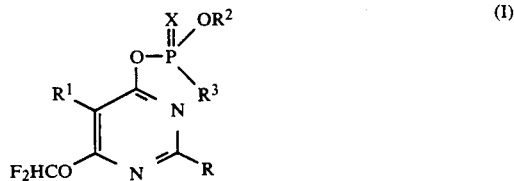

in which
R represents hydrogen, or represents an optionally substituted radical selected from the group consisting of alkyl, alkoxy, alkylthio, dialkylamino, cycloalkyl and aryl,
$R^1$ represents hydrogen, aklyl or halogen,
$R^2$ represents alkyl,
$R^3$ represents alkyl, alkoxy, alkylthio, amino, alkylamino, dialkylamino or aryl and
X represents oxygen or sulphur.

11 Claims, No Drawings

PESTICIDAL PYRIMIDINYL (THIONO) (THIO)-PHOSPHORIC (PHOSPHONIC)ACID (AMIDE) ESTERS

The invention relates to new pyrimidinyl(thiono)(thio)-phosphoric(phosphonic) acid (amide) esters, several processes for their preparation and their use as agents for combating pests, in particular as insecticides, acaricides and nematicides.

It is already known that certain pyrimidinylthionophosphoric(phosphonic) acid esters, such as, for example, 0,0-diethyl 0-(6-methyl-2-i-propyl-pyrimidin-4-yl)-thionophosphate and 0-(6-methoxy-2-t-butyl-pyrimidin-4yl) 0-methyl-thionoethanephosphonate, have a pesticidal action (compare U.S. Pat. No. 2,754,243 and DE-OS 22 09 554). However, the action and the duration of action of these known compounds is not always completely satisfactory, especially when low amounts are applied and in the case of low concentrations of active compound.

New pyrimidinyl(thiono)(thio)-phosphoric(phosphonic) acid (amide) esters of the general formula (I)

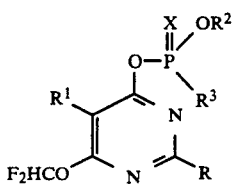

in which

R represents hydrogen, or represents an optionally substituted radical of the series comprising alkyl, alkoxy, alkylthio, dialkylamino, cycloalkyl and aryl, $R^1$ represents hydrogen, alkyl or halogen, $R^2$ represents alkyl, $R^3$ represents alkyl, alkoxy, alkylthio, amino, alkylamino, dialkylamino or aryl and X represents oxygen or sulphur, have now been found.

It has furthermore been found that the new pyrimidine(thiono)(thio)-phosphoric(phosphonic) acid (amide) esters of the general formula (I) are obtained by a process in which a) 4-difluoromethoxy-6-hydroxy-pyrimidine derivatives of the formula (II)

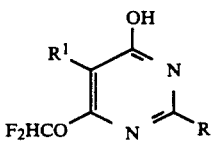

in which $R^1$ and R have the abovementioned meanings, or the corresponding alkali metal, alkaline earth metal or ammonium salts, are reacted with halides of the formula (III)

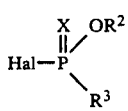

in which $R^2$, $R^3$ and X have the abovementioned meanings and Hal represents halogen, preferably chlorine or bromine, in particular chlorine, if appropriate in the presence of an acid acceptor and if appropriate in the presence of a diluent, or b) by a process in which 6-hydroxy-pyrimidine derivatives of the formula (IV)

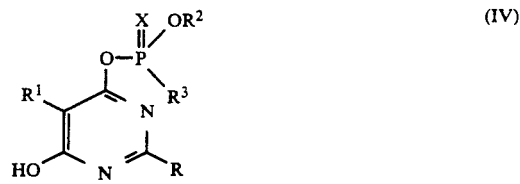

in which R, $R^1$, $R^2$, $R^3$ and X have the abovementioned meanings, or the corresponding alkali metal, alkaline earth metal or ammonium salts, are reacted with chlorodifluoromethane of the formula (V)

$$Cl-CHF_2 \qquad (V)$$

if appropriate in the presence of an acid acceptor and if appropriate in the presence of a diluent.

The new pyrimidinyl(thiono)(thio)-phosphoric(phosphonic) acid (amide) esters of the formula (I) are distinguished, surprisingly, by a particularly high activity as agents for combating pests, in particular as insecticides, acaricides and nematicides.

The substances according to the invention thus represent a useful enrichment of the art.

Preferred substituents and examples of the radicals listed in the formulae mentioned above and below are illustrated below:

In the general formulae, alkyl denotes straight-chain or branched alkyl having preferably 1 to 6 carbon atoms, preferably having 1 to 4 carbon atoms; examples which may be mentioned are methyl, ethyl, n- and i-propyl, n-, i-, s- and t-butyl, pentyl and hexyl.

The term alkoxy in the definition of R and $R^3$ in the general formulae is to be understood as meaning straight-chain or branched alkoxy having preferably 1 to 6, in particular 1 to 4, carbon atoms. Examples which may be mentioned are unsubstituted or substituted methoxy, ethoxy, propoxy, butoxy and their isomers, such as, for example, i-propoxy and i-, s- and t-butoxy.

Alkylthio in the definition of R and $R^3$ in the general formulae is straight-chain or branched alkylthio having preferably 1 to 4 carbon atoms. Methylthio, ethylthio, n- and i-propylthio and n-, i-, s- and t-butylthio are particularly preferred.

Alkyl in the alkylamino and dialkylamino groups R and $R^3$ is straight-chain or branched and in each case preferably contains 1 to 4, in particular 1 to 3, carbon atoms, methyl, ethyl and n- and i-propyl being mentioned. Examples which may be mentioned are dimethylamino, diethylamino, di-n-propylamino and di-i-propylamino.

Cycloalkyl in the definition of R represents cycloalkyl having preferably 3 to 6, in particular 3 or 6, carbon atoms.

Examples which may be mentioned are unsubstituted or substituted cyclopropyl, cyclobutyl, cyclopentyl, cyclohexyl and cycloheptyl.

The term aryl in the definition of R and $R^3$ in the general formulae is to be understood as meaning aryl having preferably 6 to 10 carbon atoms in the aryl part.

Examples which may be mentioned are unsubstituted or substituted phenyl or naphthyl, in particular phenyl.

Halogen in the definition of R represents fluorine, chlorine or bromine, in particular chlorine or bromine.

The optionally substituted radicals of the general formulae can carry one or more, preferably 1 to 3, in particular 1 or 2, identical or different substituents. Substituents which may be mentioned as examples and as preferred are: alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propoxy and n-, i- and t-butoxy; alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, the halogen atoms being identical or different and halogen atoms preferably being fluorine, chlorine or bromine, in particular fluorine, such as trifluoromethyl; hydroxyl; halogen, preferably fluorine, chlorine, bromine and iodine, in particular fluorine, chlorine and bromine; and alkylsulphonyl having preferably 1 to 4, in particular 1 or 2, carbon atoms, such as methylsulphonyl and ethylsulphonyl. The optionally substituted radicals are preferably unsubstituted.

In the general formulae, R preferably represents $C_1$–$C_4$-alkyl or $C_1$–$C_4$-alkylthio, in particular i-$C_3H_7$ or t-$C_4H_9$.

$R^1$ in the general formulae preferably represents hydrogen, $R^2$ in the general formulae preferably represents $C_1$–$C_4$-alkyl, in particular methyl, ethyl or i-propyl.

In the general formulae, $R^3$ preferably represents $C_1$–$C_4$-alkyl, $C_1$–$C_4$-alkoxy, $C_1$–$C_4$-alkylthio or $C_1$–$C_4$-alkylamino, in particular methyl, ethyl, methoxy, ethoxy or i-propylamino.

X in the general formulae preferably represents sulphur.

Preferred pyrimidinyl(thiono)(thio)-phosphoric(-phosphonic) acid (amide) esters of the formula (I) according to the invention are those in which R represents hydrogen, alkyl having 1 to 4 carbon atoms, alkyl having 1 to 4 carbon atoms which is substituted by alkylsulphonyl having 1 or 2 carbon atoms, alkoxy having 1 to 4 carbon atoms, alkylthio having 1 to 4 carbon atoms, dialkylamino having 1 to 4 carbon atoms in the individual alkyl parts, cycloalkyl having 3 to 6 carbon atoms or phenyl (preferably $C_1$–$C_4$-alkyl or $C_1$–$C_4$-alkylthio), $R^1$ represents hydrogen, alkyl having 1 to 4 carbon atoms or halogen (preferably hydrogen), $R^2$ represents alkyl having 1 to 4 carbon atoms, $R^3$ represents alkyl having 1 to 4 carbon atoms, alkoxy having 1 to 4 carbon atoms, alkylthio having 1 to 4 carbon atoms, amino, alkylamino having 1 to 4 carbon atoms, dialkylamino having 1 to 4 carbon atoms in the individual alkyl parts or phenyl (preferably $C_1$–$C_4$-alkyl, $C_1$–$C_4$-alkoxy or $C_1$–$C_4$-alkylamino) and X represents oxygen or sulphur (preferably sulphur).

Particularly preferred pyrimidinyl(thiono)(thio)phosphoric(phosphonic) acid (amide) esters of the formula (I) are those in which R represents hydrogen, methyl, ethyl, n-propyl, i-propyl, sec.-butyl, t.-butyl, methylsulphonylmethyl, methylsulphonylethyl, methoxy, ethoxy, i-propoxy, methylthio, ethylthio, i-propylthio, dimethylamino, diethylamino, cyclopropyl, cyclohexyl or phenyl (preferably i-propyl, t-butyl or methylthio), $R^1$ represents hydrogen, methyl, ethyl, chlorine or bromine (preferably hydrogen), $R^2$ represents methyl, ethyl, n-propyl, i-propyl, n-butyl, sec.-butyl, i-butyl or t-butyl (preferably methyl, ethyl or i-propyl), $R^3$ represents methyl, ethyl, methoxy, ethoxy, i-propoxy, methylthio, ethylthio, n-propylthio, sec.butylthio, amino, ethylamino, n-propylamino, i-propylamino, sec.-butylamino, dimethylamino, diethylamino or phenyl (preferably ethyl, methoxy, ethoxy or i-propylamino) and X represents oxygen or sulphur (preferably sulphur).

The preferred definitions stated for the compounds of the formula (I) also apply to the starting compounds of the formulae (II), (III) and (IV).

The compounds of the formula (I)

$$\underset{F_2HCO}{\overset{R^1}{\phantom{X}}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\! \text{(I)}$$

listed below in Table 1 may be mentioned specifically, in addition to the compounds mentioned in the preparation examples:

TABLE 1

| R | $R^1$ | $R^2$ | $R^3$ | X |
|---|---|---|---|---|
| $C_3H_7$-iso | H | $C_2H_5$ | $OC_2H_5$ | S |
| $C_3H_7$-iso | H | $CH_3$ | $OCH_3$ | S |
| $CH_3$ | H | $CH_3$ | $OCH_3$ | S |
| $CH_3$ | H | $C_2H_5$ | $OC_2H_5$ | S |
| $OCH_3$ | H | $C_2H_5$ | $OC_2H_5$ | S |
| $N(CH_3)_2$ | H | $C_2H_5$ | $OC_2H_5$ | S |
| $OCH_3$ | H | $CH_3$ | $OCH_3$ | S |
| $OCH_3$ | H | $CH_3$ | $C_2H_5$ | S |
| $C_4H_9$-tert. | Cl | $C_2H_5$ | $OC_2H_5$ | S |
| $CH_3$ | $CH_3$ | $C_2H_5$ | $OC_2H_5$ | S |
| $C_3H_7$-iso | H | $C_2H_5$ | phenyl | S |
| cyclopropyl | H | $C_2H_5$ | $OC_2H_5$ | S |
| cyclohexyl | H | $C_2H_5$ | $OC_2H_5$ | S |
| H | H | $C_2H_5$ | $OC_2H_5$ | S |
| $C_2H_5$ | H | $C_2H_5$ | $OC_2H_5$ | S |

If, for example, 2-methylthio-4-difluoromethoxy-6-hydroxypyrimidine and O,O-diethyl chlorothionophosphate are used as starting substances for process (a) according to the invention, the corresponding reaction can be outlined by the following equation:

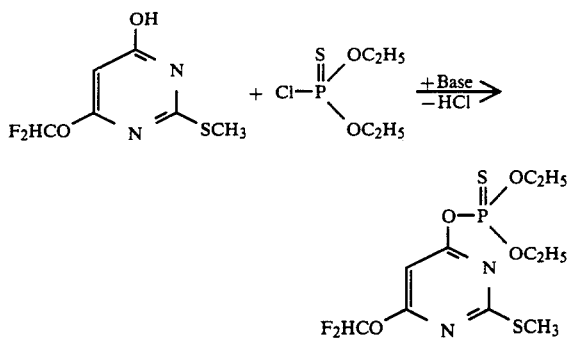

If, for example, 0-(4-hydroxy-2-tert-butyl-pyrimidin-6-yl) 0-methyl thionoethanephosphonate and chlorodifluoromethane are used as starting substances, the corresponding reaction can be outlined by the following equation:

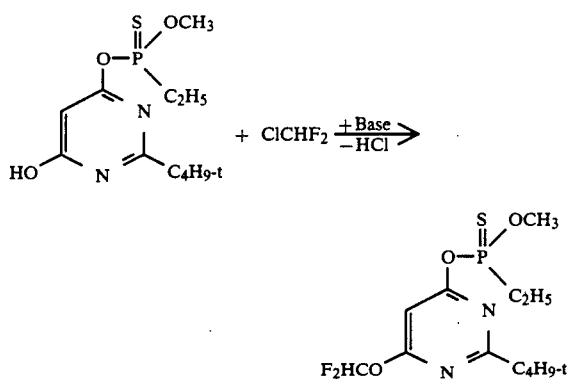

Formula (II) provides a general definition of the 4-difluoromethoxy-6-hydroxy-pyrimidine derivatives and the corresponding alkali metal, alkaline earth metal or ammonium salt to be employed as starting substances in process variant (a) according to the invention. In this formula (II), $R^1$ and R preferably represent the meaning which has already been mentioned as preferred for these substituents in the description of the substances of the formula (I) according to the invention.

The compounds of the formula (II) are known in some cases (compare, for example, U.S. Pat. No. 4,692,524) and/or they can be obtained in an analogous manner by processes which are known, for example by a process in which 4,6-dihydroxypyrimidines of the formula (VI)

in which

R has the abovementioned meaning, are reacted with chlorodifluoromethane of the formula (V)

Cl—CHF₂                      (V)

if appropriate in the presence of a diluent, such as, for example, dioxane, and if appropriate in the presence of a base, such as, for example, sodium hydroxide, at temperatures between 20° C. and 100° C.

The compounds of the formula (II)

listed below in Table 2 may be mentioned specifically, in addition to the compounds mentioned in the preparation examples:

TABLE 2

| R | $R^1$ |
|---|---|
| C₃H₇-iso | H |
| C₂H₅ | H |
| CH₃ | H |
| H | H |
| OCH₃ | H |
| N(CH₃)₂ | H |
| C₃H₇-iso | Cl |
| C₃H₇-iso | CH₃ |
| △ (cyclopropyl) | H |
| C₆H₅ (phenyl) | H |

Formula (III) provides a definition of the halides also to be employed as starting substances for carrying out process variant (a) according to the invention. In this formula, $R^2$, $R^3$ and X represent those radicals stated in the definition in formula (I). Hal in this formula represents halogen, in particular chlorine or bromine.

The compounds of the formula (III) are known and/or can be prepared by generally known processes and methods (compare, for example, Methoden der organischen Chemie (Methods of Organic Chemistry) (Houben-Weyl-Müller), 4th edition, Volume 12/1 (1963), p. 415–420 and p. 560–563, Volume 12/2 (1964), p. 274–292, p. 405–408 and p. 607–618, p. 621–622 and p. 755–757; Thieme-Verlag Stuttgart).

Examples which may be mentioned of compounds of the formula (II) are:

Methoxy-methyl-, methoxy-ethyl-, methoxy-n-propyl-, methoxy-i-propyl, methoxy-n-butyl-, methoxy-i-butyl-, methoxy-sec.-butyl-, ethoxy-methyl-, ethoxyethyl-, ethoxy-n-propyl-, ethoxy-i-propyl-, ethoxy-n-butyl-, ethoxy-i-butyl-, ethoxy-sec-butyl-, n-propoxymethyl-, n-propoxy-ethyl-, n-propoxy-n-propyl-, n-propoxy-i-propyl, n-propoxy-n-butyl-, n-propoxy-i-butyl-, i-propoxy-methyl-, i-propoxy-ethyl-, i-propoxy-n-propyl-, i-propoxy-i-propyl-, i-propoxy-n-butyl-, i-propoxy-i-butyl-, n-butoxy-methyl-, n-butoxy-ethyl-, n-butoxy-n-propyl-, n-butoxy-i-propyl-, n-butoxy-n-butyl-, n-butoxy-i-butyl-, i-butoxy-methyl-, i-butoxy-ethyl-, i-butoxy-n-propyl, i-butoxy-i-propyl, i-butoxy-n-butyl-, i-butoxy-i-butyl-, sec-butoxy-methyl-, sec-butoxy-ethyl, sec-butoxy-n-propyl-, sec-butoxy-i-propyl-, sec-butoxy-n-butyl-, sec-butoxy-i-butyl-, tert-butoxy-methyl-, tert-butoxy-ethyl, tert-butoxy-n-propyl-, tert-butoxy-i-propyl-, tert-butoxy-n-butyl- and tert-butoxy-i-butyl(thiono)phosphonic acid ester-chloride and -bromide;

Dimethoxy-, diethoxy-, di-n-propoxy-, di-i-propoxy, di-n-butoxy-, di-i-butoxy-, methoxy-ethoxy-, methoxy-n-propoxy, methoxy-i-propoxy-, methoxy-n-butoxy-, methoxy-i-butoxy-, methoxy-sec-butoxy-, methoxy-tert-butoxy-, ethoxy-n-propoxy, ethoxy-i-propoxy-, ethoxy-n-butoxy-, ethoxy-i-butoxy-, ethoxy-sec-butoxy-, ethoxy-tert-butoxy-, n-propoxy-i-propoxy-, n-propoxy-n-butoxy-, n-propoxy-i-butoxy-, n-propoxy-sec-butoxy-, n-propoxy-tert-butoxy-, i-propoxy-n-butoxy-, i-propoxy-i-butoxy, n-butoxy-i-butoxy-, n-butoxy-sec-butoxy- and n-butoxy-tert-butoxy-chloro- and bromo (thiono)phosphate;

Methoxy-methylthio-,methoxy-ethylthio-,methoxy-n-propylthio-, methoxy-i-propylthio-, methoxy-n-butylthio-, methoxy-i-butylthio-, methoxy-sec-butylthio-, ethoxy-methylthio-, ethoxy-ethylthio-, ethoxy-n-propylthio-, ethoxy-i-propylthio-, ethoxy-n-butylthio-, ethoxy-i-butylthio-, ethoxy-sec-butylthio-, n-propoxy-methylthio-, n-propoxy-ethylthio-, n-propoxy-n-propylthio-, n-propoxy-i-propylthio-, n-propoxy-n-butylthio, n-propoxy-i-butylthio-, i-propoxy-methylthio-, i-propoxy-ethylthio-, i-propoxy-n-propylthio-, i-propoxy-i-propylthio-, i-propoxy-n-butylthio-, i-propoxy-i-butylthio-,n-butoxy-methylthio-, n-butoxy-ethylthio-, n-butoxy-n-propylthio-, n-butoxy-i-propylthio-, n-butoxy-n-butylthio-, n-butoxy-i-butylthio-, i-butylthio-, i-butoxy-methylthio-, i-butoxy-ethylthio-, i-butoxy-n-propylthio-,i-butoxy-i-propylthio-, i-butoxy-n-butylthio- and i-butoxy-i-butylthio-chloro- and bromo (thiono)phosphate;

Methoxy-(di)methylamino-, methoxy-(di)ethylamino-, methoxy-(di)n-propylamino-, methoxy-(di)i-propylamino-, methoxy-(di)n-butylamino-, methoxy-(di)i-butylamino-, ethoxy-(di)methylamino-, ethoxy-(di)ethylamino-, ethoxy-(di)n-propylamino-, ethoxy-(di)i-propylamino-, ethoxy-(di)n-butylamino-, ethoxy-(di)i-butylamino-, n-propoxy-(di)methylamino-, n-propoxy-(di)ethylamino-, n-propoxy-(di)n-propylamino-, n-propoxy-(di)i-propylamino-, n-propoxy-(di)n-butylamino-, n-propoxy-(di)i-butylamino-, i-propoxy-(di)methylamino-, i-propoxy-(di)ethylamino-, i-propoxy-(di)n-propylamino-, i-propoxy-(di)i-propylamino-, i-propoxy-(di)n-butylamino-, i-propoxy-(di)i-butylamino-, n-butoxy-(di)methylamino-, n-butoxy-(di)ethylamino-, n-butoxy-(di)n-propylamino-, n-butoxy-(di)i-propylamino-, n-butoxy-(di)n-butylamino-, n-butoxy-(di)i-butylamino-, i-butoxy-(di)methylamino-, i-butoxy-(di)ethylamino-, i-butoxy-(di)n-propylamino-, i-butoxy-(di)i-propylamino-, i-butoxy-(di)n-butylamino-, i-butoxy-(di)i-butylamino-, sec-butoxy-(di)methylamino-, sec-butoxy-(di)ethylamino-, sec-butoxy-(di)n-propylamino-, sec-butoxy-(di)i-propylamino-, sec-butoxy-(di)i-butylamino-, tert-butoxy-(di)methylamino-, tert-butoxy-(di)ethylamino-, tert-butoxy-(di)n-propylamino- and tert-butoxy-(di)n-butylaminochloro- and bromo(thiono)phosphate and Methoxy-, ethoxy-, n-propoxy-, i-propoxy-, n-butoxy-, i-butoxy-, sec-butoxy- and tert-butoxy-phenyl chloro- and bromo thiono)phosphate.

Formula (IV) provides a general definition of the 6-hydrox-y-pyrimidine derivatives and the corresponding alkali metal, alkaline earth metal or ammonium salt to be employed as starting substances for carrying out process variant (b) according to the invention. In this formula (IV), R, $R^1$, $R^2$, $R^3$ and X represent the meanings which have already been mentioned as preferred for these substituents in the description of the substances of the formula (I) according to the invention.

The compounds of the formula (IV) are known (compare, for example, DE-OS (German Published Specification) 3,704,689 and DE-OS (German Published Specification) 2,630,054), and/or can be obtained in an analogous manner by known processes, for example by a process in which 4,6-dihydroxypyrimidines of the formula (VI)

in which R has the abovementioned meaning, are reacted with halides of the formula (III)

in which $R^2$, $R^3$ and X have the abovementioned meanings and Hal represents halogen, preferably chlorine or bromine, in particular chlorine, if appropriate in the presence of a diluent, such as, for example, methylene chloride, and if appropriate in the presence of a base, such as, for example, triethylamine, at temperatures between 0° C. and 50° C.

The chlorodifluoromethane of the formula (V) also to be used as a starting substance for carrying out process variant (b) according to the invention is a generally known compound of organic chemistry.

Process variant (a) for the preparation of the compounds of the general formula (I) is preferably carried out also using suitable solvents and diluents. Possible solvents and diluents are virtually all the inert organic solvents. These include, in particular, aliphatic and aromatic, optionally chlorinated hydrocarbons, such as benzene, toluene, xylene, benzine, methylene chloride, chloroform, carbon tetrachloride and chlorobenzene, or ethers, such as diethyl ether, dibutyl ether, tetrahydrofuran and dioxane, and furthermore ketones, for example acetone, methyl ethyl ketone, methyl isopropyl ketone and methyl isobutyl ketone, and in addition nitriles, such as acetonitrile and propionitrile.

Acid acceptors which can be used are all the customary acid-binding agents. Acid acceptors which have proved to be particularly appropriate are alkali metal carbonates and alcoholates, such as sodium carbonate and potassium carbonate and potassium tert.-butylate, and furthermore aliphatic, aromatic or heterocyclic amines, for example triethylamine, trimethylamine, dimethylaniline, dimethylbenzylamine and pyridine.

The reaction temperature can be varied within a substantial range. The reaction is in general carried out between 0° C. and 100° C., preferably at 20° C. to 60° C.

The reaction is in general allowed to proceed under normal pressure.

The starting materials are usually employed in an equivalent ratio for carrying out process variant (a). An excess of one or the other of the components provides no substantial advantages. The reaction partners are usually combined in one of the abovementioned solvents in the presence of an acid-binding agent and are stirred at elevated temperature for one or more hours in order to bring the reaction to completion. An organic solvent, for example toluene, is then added to the mixture and the organic phase is worked up in the customary manner by washing, drying and distilling off the solvent.

Process variant (b) for the preparation of the compounds of the general formula (I) is likewise preferably carried out also using suitable solvents and diluents. Possible solvents and diluents are virtually all the inert organic solvents. These include, in particular, aliphatic and aromatic, optionally chlorinated hydrocarbons, such as benzene, toluene, xylene, benzine, methylene chloride, chloroform, carbon tetrachloride and chlorobenzene, or ethers, such as diethyl ether, dibutyl ether, tetrahydrofuran and dioxane, and furthermore ketones, for example acetone, methyl ethyl ketone, methyl isopropyl ketone and methyl isobutyl ketone, and in addition nitriles, such as aceto- and propionitrile.

All the customary acid-binding agents can be used as acid acceptors. Acid-binding agents which have proved particularly appropriate are alkali metal hydroxides and alkali metal carbonates and alcoholates, such as sodium hydroxide and potassium hydroxide, sodium carbonate and potassium carbonate and potassium tert-butylate, and furthermore aliphatic, aromatic or heterocyclic amines, for example triethylamine, trimethylamine, dimethylaniline, dimethylbenzylamine and pyridine.

The reaction temperature can be varied within a substantial range. The reaction is in general carried out between $-20°$ C. and $+60°$ C., preferably at $-10°$ C. to $+40°$ C.

The reaction is in general allowed to proceed under normal pressure. However, it is also possible to carry out the reaction under pressure (preferably 1-10 bar).

The starting materials are preferably employed in an equivalent ratio for carrying out process variant (b). However, it is also possible for the chlorodifluoromethane used as a reaction partner to be employed in excess. The reaction partners are usually combined in one of the abovementioned solvents in the presence of an acid-binding agent and stirred for one or more hours in order to bring the reaction to completion. The reaction mixture is then filtered and the solvent is distilled off under reduced pressure.

The compounds of the general formula (I) are usually obtained in the form of oils which often cannot be distilled without decomposition, but can be freed from the last volatile constituents by so-called "incipient distillation", that is to say by prolonged heating to a moderately elevated temperature under reduced pressure, and can be purified in this manner. They are characterized by their refractive index.

The active compounds are suitable for controlling animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp.. From the order of the Anoplura, for example, *Phylloxera vastatrix*, Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp. *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varive stis*, Atomaria spp., *Oryzaephilus surinamensis*, Antho nomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctuc spp., *Meligethes aeneus*, Ptinus spp., *Niptus hololeucus, Gibbium psylloides*, Tribolium spp., *Tenebrio molitor*, Agriotes spp., Cono derus spp., *Melolontha melolontha, Amph-imallon solsti tialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*. From the order of the Siphonaptera, for example, *Xenopsylla cheopis* and Ceratophyllus spp. From the order of the Arachnida, for example, Scorpio maurus and *Latrodectus mactans*.

From the order of the Acarina, for example, Acarus siro, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp. and Trichodorus spp.

The active compounds of the formula (I) according to the invention are distinguished in particular by an outstanding insecticidal and nematicidal activity. They exhibit an outstanding action in particular when used as leaf insecticides and soil insecticides, in particular against larvae, such as, for example, *Diabrotica balteata* larvae, against aphids, such as Aphis fabae, against nematodes, such as *Globodera rostochiensis*, and against caterpillars, such as *Spodoptera frugiperda*. They are also particularly suitable for seed treatment.

Some of the substances according to the invention moreover also exhibit a fungicidal action against *Pyricularia oryzae* and *Pellicularia sasakii* on rice.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds can present in their commercially available formulations and in the use forms, prepared from these formulations, in a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds can furthermore be present in their commercially available formulations and in the use forms prepared from these formulations, in a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The preparation and use of the active compounds according to the invention is illustrated by the following examples.

In the present text, all percentage data relate to percentages by weight, unless stated otherwise.

PREPARATION EXAMPLES

Example 1

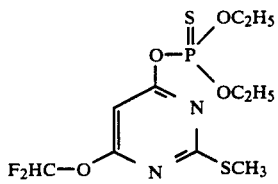

Process variant (a)

A. mixture of 80 ml of acetonitrile, 20.8 g (0.1 mol) of 2-methylthio-4-difluoromethoxy-6-hydroxypyrimidine, 20.7 g (0.15 mol) of potassium carbonate and 18.8 g (0.1 mol) of 0,0-diethyl chlorothionophosphate is stirred at 55° C. for 2 hours. The reaction mixture is then poured into 400 ml of toluene and washed twice with 300 ml of water each time. The toluene solution is dried over sodium sulphate and evaporated under reduced pressure. The residue is subjected to incipient distillation under a high vacuum.

29 g (81% of theory) of 0,0-diethyl 0-(2-methylthio-4-difluoromethoxy-pyrimidin-6-yl) thionophosphate are thus obtained in the form of colorless crystals of melting point 39° C.

Example 2

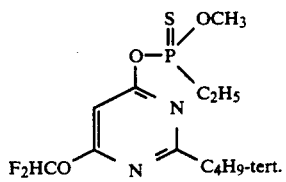

Process variant (b)

14.5 g (0.05 mol) of 0-(4-hydroxy-2-tert-butylpyrimidin-6-yl) 0-methylthionoethanephosphonate are added to a solution of 6.7 g (0.06 mol) of potassium tertbutylate in 100 ml of dry tetrahydrofuran, while cooling with ice. Chlorodifluoromethane is passed into this mixture at $-5°$ to $0°$ C. in the course of 2 hours and the mixture is then stirred at room temperature for 18 hours. The solvent is subsequently stripped off under reduced pressure; the residue is dissolved in 500 ml of n-hexane, 15 g of silica gel are added and the mixture is filtered. The filtrate is evaporated under reduced pressure and the residue is subjected to incipient distillation under a high vacuum at 30° C.

6.9 g (41% of theory) of 0-(4-difluoromethoxy-2-tert-butyl-pyrimidin-6-yl) 0-methylthionoethanephosphonate are thus obtained in the form of a colorless oil of refractive index $n_D^{24}$: 1.4853.

The end products of the formula (I)

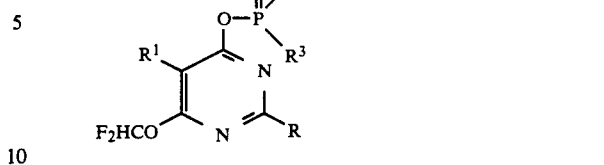

listed below in Table 3 are obtained in an analogous manner to Examples 1 and 2 and taking into account the information in the description of the processes according to the invention.

TABLE 3

| Example No. | R | $R^1$ | $R^2$ | $R^3$ | X | Refractive index |
|---|---|---|---|---|---|---|
| 3 | $C_4H_9$-tert | H | $C_2H_5$ | $OC_2H_5$ | S | $n_D^{24}$: 1.4780 |
| 4 | $C_4H_9$-tert | H | $CH_3$ | $OCH_3$ | S | $n_D^{22}$: 1.4834 |
| 5 | $C_4H_9$-tert | H | $C_2H_5$ | $NHC_3H_7$-iso | S | $n_D^{23}$: 1.4872 |
| 6 | $C_4H_9$-tert | H | $C_3H_7$-iso | $OC_2H_5$ | S | $n_D^{22}$: 1.4751 |
| 7 | $C_4H_9$-tert | H | $C_2H_5$ | $SC_4H_9$-sec | O | $n_D^{22}$: 1.4835 |
| 8 | $C_3H_7$-iso | H | $C_2H_5$ | $OC_2H_5$ | S | $n_D^{22}$: 1.4835 |
| 9 | $C_3H_7$-iso | H | $CH_3$ | $OCH_3$ | S | $n_D^{23}$: 1.4890 |

Preparation of the starting substances

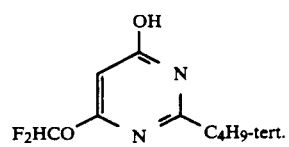

Chlorodifluoromethane is passed into a mixture of 84 g (0.5 mol) of 2-tert-butyl-4,6-dihydroxypyrimidine, 100 ml of dioxane, 90 ml of water and 80 g (2 mol) of sodium hydroxide at 80° C., until all the precursor has reacted. After addition of 1 l of water, the mixture is brought to pH 6 with concentrated hydrochloric acid, while cooling, and the product which has precipitated is filtered off with suction.

63.7 g (29% of theory) of 2-tert-butyl-4-difluoromethoxy-6-hydroxypyrimidine are obtained in this manner in the form of colorless crystals of melting point 156° C.

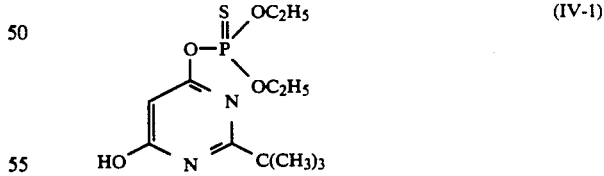

A mixture of 21.1 g (0.125 mol) of 4,6-dihydroxy-2-tert-butyl-pyrimidine, 13.3 g (0.131 mol) of triethylamine and 120 ml of methylene chloride is stirred at 20° C. for 30 minutes and then cooled to 5° C., and 19.7 g (0.105 mol) of 0,0-diethyl chloro thionophosphate are added dropwise. The reaction mixture is stirred at 20° C. for 20 hours, washed twice with 50 ml of water each time and evaporated under a water pump vacuum.

19.9 g 60% of theory) of 0,0-diethyl 0-(4-hydroxy-2-tert-butyl-pyrimidin-6-yl) thionophosphate are thus obtained as a crystalline residue of melting point 98° C.

The intermediate products of the formula (IV)

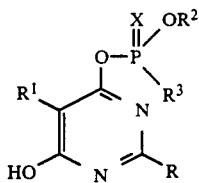

listed below in Table 4 are obtained in an analogous manner to Example (IV-1) and taking into account the information in the description of the processes according to the invention:

TABLE 4

| Example No. | R | $R^1$ | $R^2$ | $R^3$ | X | Refractive index |
|---|---|---|---|---|---|---|
| (IV-2) | $C_4H_9$-tert | H | $C_2H_5$ | $-S-CH(CH_3)-C_2H_5$ | O | $n_D^{22}$: 1.5275 |
| (IV-3) | $C_4H_9$-tert | H | $C_2H_5$ | $-NH-C_3H_7$-iso | S | $n_D^{22}$: 1.5332 |

Use Examples

The compounds shown below are employed as comparison substances in some of the use examples which follow:

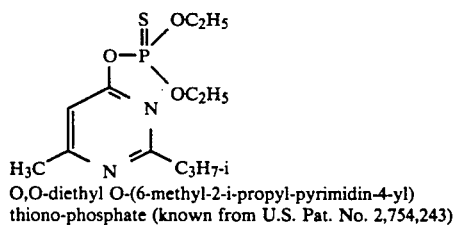

O,O-diethyl O-(6-methyl-2-i-propyl-pyrimidin-4-yl) thiono-phosphate (known from U.S. Pat. No. 2,754,243)

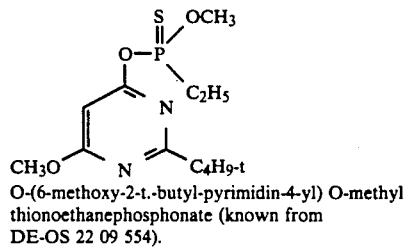

O-(6-methoxy-2-t.-butyl-pyrimidin-4-yl) O-methyl thionoethanephosphonate (known from DE-OS 22 09 554).

Example A

Test insect: *Diabrotica balteata*—larvae in the soil
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with soil. The concentration of the active compound in the preparation is of practically no importance here, only the amount by weight of active compound per unit volume of soil, which is given in ppm (mg/1), being decisive. The soil is transferred into 0.5 1 pots and the pots are left to stand at 20° C.

Immediately after preparation, 6 pregerminated corn grains are placed in each pot. After 2 days, the corresponding test insects are placed in the treated soil. After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the compounds of Examples (1) and (2) exhibited a degree of destruction of 95% at a concentration of, for example, 0.3 ppm, whereas comparison compound (B) resulted in no destruction (0%) at the same concentration.

Example B

Seed treatment test/soil insects

Test insect: *Diabrotica balteata*—larvae in the soil
Test plant: *Zea mays*
Solvent: 1 part by weight of acetone
Excipient: kaolin To produce a suitable preparation of active compound, the active compound is dissolved in acetone and 1 part by weight of active compound/acetone is mixed with 5 parts by weight of kaolin. The corn seeds are treated with this active compound preparation at the application rates required. They are sown in 0.5 1 pots containing standardized soil at a room temperature of 20° C.

After 1 day, about 30 Diabrotica larvae are placed in each pot. After a further 7 days, the degree of effectiveness of the active compound is determined in % by counting the dead and live test insects. The degree of effectiveness is 100% if all the test insects have been killed and is 0% if just as many test insects are still alive as in the case of the untreated control.

In this test, the compounds of Examples (2) and (5) exhibited a degree of destruction of 100% at a concentration of, for example, 1 g/kg, whereas comparison compound (A) resulted in no destruction (0%) at the same concentration.

Example C

Test nematode: *Globodera rostochiensis*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil heavily infested with the test nematodes. The concentration of the active compound in the preparation is of practically no importance here, only the amount of active compound per unit volume of soil, which is given in ppm, being decisive. The treated soil is transferred into pots, potatoes are planted and the pots are kept at a greenhouse temperature of 18° C.

After six weeks, the potato roots are examined for cysts and the degree of effectiveness of the active compound is determined in %. The degree of effectiveness is 100% if infestation is avoided completely, and is 0% if the infestation is just as high as in the control plants in untreated but similarly infested soil.

17

In this test, the compound of Example (3) exhibited a degree of destruction of 95% at a concentration of, for example, 2.5 ppm, whereas comparison compound (B) resulted in no destruction (0%) at the same concentration.

Example D

Aphis test (systemic action)

Solvent: 7 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added, and the concentrate is diluted with water to the desired concentration.

Bean plants (Vicia faba) which have been heavily infested with the black bean aphid (Aphis fabae) are each watered with 20 ml of the preparation of the active compound of the desired concentration in such a way that the preparation of the active compound penetrates into the soil without wetting the shoot. The active compound is taken up by the roots and passes to the shoot.

After the specified period of time, the destruction in % is determined. Here 100% means that all the aphids have been killed; 0% means that none of the aphids have been killed.

In this test, the compounds of Examples (3) and (4) exhibited a degree of destruction of 100% after 4 days at a concentration of, for example, 0.1%, whereas comparison compound (B) resulted in no destruction (0%) at the same concentration.

Example E

Spodoptera test

Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*), while the leaves are still moist.

After the specified period of time, the destruction in % is determined. Here 100% means that all the caterpillars have been killed; 0% means that none of the caterpillars have been killed.

In this test, the compound of Example (4) exhibited a degree of destruction of 100% after 3 days at a concentration of, for example, 0.001%, whereas comparison compound (A) resulted in no destruction (0%) at the same concentration.

It will be appreciated that the instant specification and claims are set forth by way of illustration and not limitation, and that various modifications and changes may be made without departing from the spirit and scope of the present invention.

What is claimed is:

1. A pyrimidine(thiono)(thio)-phosphoric(phosphonic) acid (amide) ester of the formula

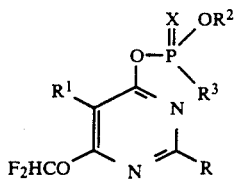

(I)

in which
R represents hydrogen, alkyl having 1 to 4 carbon atoms, alkyl having 1 to 4 carbon atoms which is substituted by alkylsulphonyl having 1 to 2 carbon atoms, alkoxy having 1 to 4 carbon atoms, alkylthio having 1 to 4 carbon atoms, dialkylamino having 1 to 4 carbon atoms in the individual alkyl parts, cycloalkyl having 3 to 6 carbon atoms or phenyl,
$R^1$ represents hydrogen, alkyl having 1 to 4 carbon atoms or halogen,
$R^2$ represents alkyl having 1 to 4 carbon atoms,
$R^3$ represents alkyl having 1 to 4 carbon atoms, alkoxy having 1 to 4 carbon atoms, alkylthio having 1 to 4 carbon atoms, amino, alkylamino having 1 to 4 carbon atoms, dialkylamino having 1 to 4 carbon atoms in the individual alkyl parts or phenyl and
X represents oxygen or sulphur.

2. A pyrimidine(thiono)(thio)-phosphoric(phosphonic) acid (amide) ester according to claim 1, in which
R represents hydrogen, methyl, ethyl, n-propyl, i-propyl, sec.-butyl, t.-butyl, methylsulphonylmethyl, methylsulphonylethyl, methoxy, ethoxy, i-propoxy, methylthio, ethylthio, i-propylthio, dimethylamino, diethylamino, cyclopropyl, cyclohexyl or phenyl,
$R^1$ represents hydrogen, methyl, ethyl, chlorine or bromine,
$R^2$ represents ethyl, ethyl, n-propyl, i-propyl, n-butyl, sec.-butyl, i-butyl or t-butyl,
$R^3$ represents methyl, ethyl, methoxy, ethoxy, i-propoxy, methylthio, ethylthio, n-propylthio, sec.butylthio, amino, ethylamino, n-propylamino, i-propylamino, sec.-butylamino, dimethylamino, di-ethylamino or phenyl and
X represents oxygen or sulphur.

3. A compound according to claim 1. in which
X represents sulphur.

4. A compound according to claim 1, wherein such compound is 0,0-diethyl 0-(2-methylthio-4-difluoromethoxypyrimidin-6-yl) thionophosphate of the formula

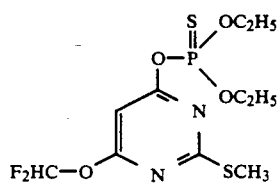

5. A compound according to claim 1, wherein such compound is 0-(4-difluoromethoxy-2-tert-butyl-pyrimidin-6-yl) 0-methylthionoethanephosphonate of the formula

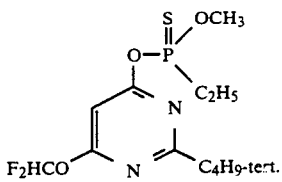

6. A compound according to claim 1, wherein such compound is O,O-diethyl O-(2-tert.-butyl-4-difluoromethoxypyrimidin-6-yl) thionophosphate of the formula

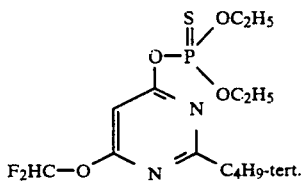

7. A compound according to claim 1, wherein such compound is O,O-dimethyl O-(2-tert.-butyl-4-difluoromethoxypyrimidin-6-yl) thionophosphate of the formula

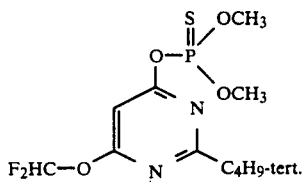

8. A compound according to claim 1, wherein such compound is O-ethyl O-(2-tert.-butyl-4-difluoromethoxypyrimidin-6-yl) N-isopropyl-thionophosphoric acid amidate of the formula

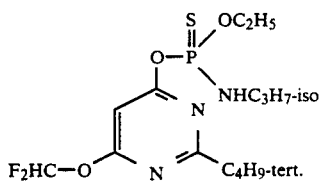

9. An insecticidal, acaricidal or nematicidal composition comprising an insecticidally, acaricidally or nematicidally effective amount of a compound according to claim 1 and a diluent.

10. A method of combating insects, acarids or nematodes which comprises applying to such insects, acarids or nematodes or to an insect, acarid or nematode habitat an insecticidally, acaricidally or nematicidally effective amount of a compound according to claim 1.

11. The method according to claim 10, wherein such compound is
O,O-diethyl O-(2-methylthio-4-difluoromethoxypyrimidin-6-yl) thionophosphate,
O-(4-difluoromethoxy-2-tert.-butyl-pyrimidin-6-yl) O-methylthionoethanephosphonate,
O,O-diethyl O-(2-tert.-butyl-4-difluoromethoxypyrimidin-6-yl) thionophosphate,
O,O-dimethyl O-(2-tert.-butyl-4-difluoromethoxypyrimidin-6-yl) thionophosphate, or
O-ethyl O-(2-tert.-butyl-4-difluoromethoxypyrimidin-6-yl) N-isopropyl-thionophosphoric acid amidate.

* * * * *